(12) United States Patent
Chu et al.

(10) Patent No.: US 12,171,486 B2
(45) Date of Patent: Dec. 24, 2024

(54) DEVICES AND METHODS FOR CLIP SEPARATION

(71) Applicant: Evalve, Inc., Santa Clara, CA (US)

(72) Inventors: Alexander Chu, Diamond Bar, CA (US); Gabriel R. Gonzales, Milpitas, CA (US); Richard Thomas Childs, San Francisco, CA (US)

(73) Assignee: Evalve, Inc., Santa Clara, CA (US)

(*) Notice: Subject to any disclaimer, the term of this patent is extended or adjusted under 35 U.S.C. 154(b) by 50 days.

(21) Appl. No.: 17/306,401

(22) Filed: May 3, 2021

(65) Prior Publication Data

US 2021/0346090 A1  Nov. 11, 2021

Related U.S. Application Data

(60) Provisional application No. 63/020,671, filed on May 6, 2020.

(51) Int. Cl.
*A61B 18/14* (2006.01)
*A61B 17/128* (2006.01)
(Continued)

(52) U.S. Cl.
CPC ...... *A61B 18/1492* (2013.01); *A61B 17/1285* (2013.01); *A61M 25/0136* (2013.01);
(Continued)

(58) Field of Classification Search
CPC ............ A61B 18/1492; A61B 17/1285; A61B 2018/00059; A61B 2018/00369;
(Continued)

(56) References Cited

U.S. PATENT DOCUMENTS

| 1,996,261 A | 4/1935 | Storz |
| 2,097,018 A | 10/1937 | Chamberlin |

(Continued)

FOREIGN PATENT DOCUMENTS

| CN | 1469724 A | 1/2004 |
| CN | 102770080 A | 11/2012 |

(Continued)

OTHER PUBLICATIONS

Nishimura, et al. 2014 AHA/ACC guideline for the management of patients with valvular heart disease: executive summary: a report of the American College of Cardiology/American Heart Association Task Force on Practice Guidelines. J Am Coll Cardiol. Jun. 10, 2014; 63(22):2438-88.

(Continued)

*Primary Examiner* — Linda C Dvorak
*Assistant Examiner* — Abigail Bock
(74) *Attorney, Agent, or Firm* — Workman Nydegger

(57) ABSTRACT

A device configured to cut leaflet tissue at a cardiac valve may comprise a guide catheter having a proximal end and a distal end, the guide catheter being positionable at a cardiac valve. The device may further include a cutting mechanism routable through the guide catheter and configured to extend from the distal end of the guide catheter, the cutting mechanism configured to cut a portion of leaflet tissue of the cardiac valve. Finally, the device may comprise a handle coupled to the proximal end of the guide catheter, the handle comprising at least one control operatively connected to the cutting mechanism such that the at least one control is configured to provide selective actuation of the cutting mechanism.

18 Claims, 5 Drawing Sheets

(51) Int. Cl.
*A61B 18/00* (2006.01)
*A61M 25/01* (2006.01)

(52) U.S. Cl.
CPC .............. *A61B 2018/00059* (2013.01); *A61B 2018/00369* (2013.01); *A61B 2018/00601* (2013.01); *A61B 2018/144* (2013.01); *A61M 25/0147* (2013.01)

(58) Field of Classification Search
CPC ... A61B 2018/00601; A61B 2018/144; A61M 25/0136; A61M 25/0147
See application file for complete search history.

(56) References Cited

U.S. PATENT DOCUMENTS

| | | |
|---|---|---|
| 2,108,206 A | 2/1938 | Mecker |
| 3,296,668 A | 1/1967 | Aiken |
| 3,378,010 A | 4/1968 | Codling et al. |
| 3,470,875 A | 10/1969 | Johnson |
| 3,557,780 A | 1/1971 | Sato |
| 3,671,979 A | 6/1972 | Moulopoulos |
| 3,675,639 A | 7/1972 | Cimber |
| 3,776,237 A | 12/1973 | Hill et al. |
| 3,874,338 A | 4/1975 | Happel |
| 3,874,388 A | 4/1975 | King et al. |
| 4,007,743 A | 2/1977 | Blake |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,312,337 A | 1/1982 | Donohue |
| 4,425,908 A | 1/1984 | Simon |
| 4,458,682 A | 7/1984 | Cerwin |
| 4,484,579 A | 11/1984 | Meno et al. |
| 4,487,205 A | 12/1984 | Di et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,872,455 A | 10/1989 | Pinchuk et al. |
| 4,878,495 A | 11/1989 | Grayzel |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox et al. |
| 5,042,707 A | 8/1991 | Taheri |
| 5,047,041 A | 9/1991 | Samuels |
| 5,049,153 A | 9/1991 | Nakao et al. |
| 5,053,043 A | 10/1991 | Gottesman et al. |
| 5,061,277 A | 10/1991 | Carpentier et al. |
| 5,069,679 A | 12/1991 | Taheri |
| 5,071,428 A | 12/1991 | Chin et al. |
| 5,078,722 A | 1/1992 | Stevens |
| 5,078,723 A | 1/1992 | Dance et al. |
| 5,108,368 A | 4/1992 | Hammerslag et al. |
| 5,125,758 A | 6/1992 | Dewan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,217,460 A | 6/1993 | Knoepfler |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,336,227 A | 8/1994 | Nakao et al. |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Krauter et al. |
| 5,368,564 A | 11/1994 | Savage |
| 5,368,601 A | 11/1994 | Sauer et al. |
| 5,373,854 A | 12/1994 | Kolozsi |
| 5,383,886 A | 1/1995 | Kensey et al. |
| 5,387,219 A | 2/1995 | Rappe |
| 5,391,182 A | 2/1995 | Chin |
| 5,395,030 A | 3/1995 | Kuramoto et al. |
| 5,403,312 A | 4/1995 | Yates et al. |
| 5,403,326 A | 4/1995 | Harrison et al. |
| 5,411,552 A | 5/1995 | Andersen et al. |
| 5,417,684 A | 5/1995 | Jackson et al. |
| 5,417,699 A | 5/1995 | Klein et al. |
| 5,417,700 A | 5/1995 | Egan |
| 5,423,830 A | 6/1995 | Schneebaum et al. |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,472,423 A | 12/1995 | Gronauer |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,584,803 A | 12/1996 | Stevens et al. |
| 5,593,424 A | 1/1997 | Northrup, III |
| 5,593,435 A | 1/1997 | Carpentier et al. |
| 5,609,598 A | 3/1997 | Laufer et al. |
| 5,617,854 A | 4/1997 | Munsif |

(56) References Cited

U.S. PATENT DOCUMENTS

| | | |
|---|---|---|
| 5,618,306 A | 4/1997 | Roth et al. |
| 5,620,452 A | 4/1997 | Yoon |
| 5,620,461 A | 4/1997 | Muijs et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,669,919 A | 9/1997 | Sanders et al. |
| 5,690,671 A | 11/1997 | Mcgurk et al. |
| 5,695,504 A | 12/1997 | Gifford et al. |
| 5,695,505 A | 12/1997 | Yoon |
| 5,702,825 A | 12/1997 | Keita et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racenet et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,271 A | 4/1998 | Nakao et al. |
| 5,741,280 A | 4/1998 | Fleenor |
| 5,746,747 A | 5/1998 | Mckeating |
| 5,749,828 A | 5/1998 | Yeung |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,591 A | 10/1998 | Thompson et al. |
| 5,820,592 A | 10/1998 | Hammerslag |
| 5,820,630 A | 10/1998 | Lind |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,843,103 A | 12/1998 | Wulfman |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,614 A | 1/1999 | Stevens et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson et al. |
| 5,895,404 A | 4/1999 | Ruiz |
| 5,895,417 A | 4/1999 | Pomeranz et al. |
| 5,906,620 A | 5/1999 | Nakao et al. |
| 5,908,420 A | 6/1999 | Parins et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhardt et al. |
| 5,957,973 A | 9/1999 | Quiachon et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 5,997,547 A | 12/1999 | Nakao et al. |
| 6,007,546 A | 12/1999 | Snow et al. |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,033,419 A | 3/2000 | Hamblin et al. |
| 6,036,699 A | 3/2000 | Andreas et al. |
| 6,048,351 A | 4/2000 | Gordon et al. |
| 6,053,933 A | 4/2000 | Balazs et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,090,118 A | 7/2000 | McGuckin, Jr. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,665 A | 9/2000 | Kawano |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,139,508 A | 10/2000 | Simpson et al. |
| 6,143,024 A | 11/2000 | Campbell et al. |
| 6,159,240 A | 12/2000 | Sparer et al. |
| 6,162,233 A | 12/2000 | Williamson et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,174,322 B1 | 1/2001 | Schneidt |
| 6,180,059 B1 | 1/2001 | Divino et al. |
| 6,182,664 B1 | 2/2001 | Cosgrove |
| 6,187,003 B1 | 2/2001 | Buysse et al. |
| 6,190,408 B1 | 2/2001 | Melvin |
| 6,197,043 B1 | 3/2001 | Davidson |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,264,617 B1 | 7/2001 | Bales et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,334,860 B1 | 1/2002 | Dorn |
| 6,352,708 B1 | 3/2002 | Duran et al. |

(56) References Cited

U.S. PATENT DOCUMENTS

| | | |
|---|---|---|
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,640 B1 | 7/2002 | Taylor |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,494,881 B1 | 12/2002 | Bales et al. |
| 6,508,828 B1 | 1/2003 | Akerfeldt et al. |
| 6,517,550 B1 | 2/2003 | Konya et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,921 B2 | 9/2003 | Blatter et al. |
| 6,626,930 B1 | 9/2003 | Allen et al. |
| 6,629,534 B1 | 10/2003 | St et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Horner |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,932,810 B2 | 8/2005 | Ryan |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen et al. |
| 7,011,669 B2 | 3/2006 | Kimblad |
| 7,033,390 B2 | 4/2006 | Johnson et al. |
| 7,048,754 B2 | 5/2006 | Martin et al. |
| 7,056,294 B2 | 6/2006 | Khairkhahan et al. |
| 7,112,207 B2 | 9/2006 | Allen et al. |
| 7,226,467 B2 | 6/2007 | Lucatero |
| 7,258,694 B1 | 8/2007 | Choi et al. |
| 7,288,097 B2 | 10/2007 | Seguin |
| 7,291,168 B2 | 11/2007 | Macoviak et al. |
| 7,338,467 B2 | 3/2008 | Lutter |
| 7,381,210 B2 | 6/2008 | Zarbatany et al. |
| 7,435,257 B2 | 10/2008 | Lashinski et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,666,204 B2 | 2/2010 | Thornton et al. |
| 7,955,340 B2 | 6/2011 | Michlitsch et al. |
| 8,216,234 B2 | 7/2012 | Long |
| 8,257,356 B2 | 9/2012 | Bleich et al. |
| 8,398,708 B2 | 3/2013 | Meiri et al. |
| 8,435,237 B2 | 5/2013 | Bahney |
| 8,496,655 B2 | 7/2013 | Epp et al. |
| 8,500,768 B2 | 8/2013 | Cohen |
| 8,523,881 B2 | 9/2013 | Cabiri et al. |
| 8,623,077 B2 | 1/2014 | Cohn |
| 8,690,858 B2 | 4/2014 | Machold et al. |
| 8,821,518 B2 | 9/2014 | Saliman et al. |
| 8,926,588 B2 | 1/2015 | Berthiaume et al. |
| 9,126,032 B2 | 9/2015 | Khairkhahan et al. |
| 9,211,119 B2 | 12/2015 | Hendricksen et al. |
| 9,370,341 B2 | 6/2016 | Ceniccola et al. |
| 9,498,331 B2 | 11/2016 | Chang et al. |
| 9,572,666 B2 | 2/2017 | Basude et al. |
| 9,770,256 B2 | 9/2017 | Cohen et al. |
| 9,949,833 B2 | 4/2018 | McCleary et al. |
| 10,238,493 B1 | 3/2019 | Metchik et al. |
| 10,667,804 B2 | 6/2020 | Basude et al. |
| 11,013,554 B2 | 5/2021 | Coates |
| 11,406,250 B2 | 8/2022 | Saadat et al. |
| 2001/0002445 A1 | 5/2001 | Vesely |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2001/0044635 A1 | 11/2001 | Niizeki et al. |
| 2002/0013547 A1 | 1/2002 | Paskar |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hlavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0173811 A1 | 11/2002 | Tu et al. |
| 2002/0173841 A1 | 11/2002 | Ortiz et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |

(56) References Cited

U.S. PATENT DOCUMENTS

| | | |
|---|---|---|
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St et al. |
| 2004/0015232 A1 | 1/2004 | Shu et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030319 A1 | 2/2004 | Korkor et al. |
| 2004/0030382 A1 | 2/2004 | St et al. |
| 2004/0034380 A1 | 2/2004 | Woolfson et al. |
| 2004/0039442 A1 | 2/2004 | St et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0059345 A1 | 3/2004 | Nakao et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092858 A1 | 5/2004 | Wilson et al. |
| 2004/0092962 A1 | 5/2004 | Thornton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0116848 A1 | 6/2004 | Gardeski et al. |
| 2004/0116951 A1 | 6/2004 | Rosengart |
| 2004/0122448 A1 | 6/2004 | Levine |
| 2004/0127849 A1 | 7/2004 | Kantor |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133232 A1 | 7/2004 | Rosenbluth et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0147826 A1 | 7/2004 | Peterson |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Liska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225233 A1 | 11/2004 | Frankowski et al. |
| 2004/0225300 A1 | 11/2004 | Goldfarb et al. |
| 2004/0225305 A1 | 11/2004 | Ewers et al. |
| 2004/0225353 A1 | 11/2004 | McGuckin et al. |
| 2004/0236354 A1 | 11/2004 | Seguin |
| 2004/0242960 A1 | 12/2004 | Orban |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Rahdert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St et al. |
| 2005/0021057 A1 | 1/2005 | St et al. |
| 2005/0021058 A1 | 1/2005 | Negro |
| 2005/0033446 A1 | 2/2005 | Deem et al. |
| 2005/0038383 A1 | 2/2005 | Kelley et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0065453 A1 | 3/2005 | Shabaz et al. |
| 2005/0085903 A1 | 4/2005 | Lau |
| 2005/0119735 A1 | 6/2005 | Spence et al. |
| 2005/0131438 A1 | 6/2005 | Cohn |
| 2005/0143809 A1 | 6/2005 | Salahieh et al. |
| 2005/0149014 A1 | 7/2005 | Hauck et al. |
| 2005/0159763 A1 | 7/2005 | Mollenauer et al. |
| 2005/0159810 A1 | 7/2005 | Filsoufi |
| 2005/0192633 A1 | 9/2005 | Montpetit |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0256452 A1 | 11/2005 | Demarchi et al. |
| 2005/0267493 A1 | 12/2005 | Schreck et al. |
| 2005/0273160 A1 | 12/2005 | Lashinski et al. |
| 2005/0277876 A1 | 12/2005 | Hayden |
| 2005/0287493 A1 | 12/2005 | Novak et al. |
| 2006/0004247 A1 | 1/2006 | Kute et al. |
| 2006/0009759 A1 | 1/2006 | Chrisitian |
| 2006/0015003 A1 | 1/2006 | Moaddes et al. |
| 2006/0015179 A1 | 1/2006 | Bulman-Fleming et al. |
| 2006/0020275 A1 | 1/2006 | Goldfarb et al. |
| 2006/0020327 A1 | 1/2006 | Lashinski et al. |
| 2006/0020334 A1 | 1/2006 | Lashinski et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0074484 A1 | 4/2006 | Huber |
| 2006/0089671 A1 | 4/2006 | Goldfarb et al. |
| 2006/0089711 A1 | 4/2006 | Dolan |
| 2006/0135961 A1 | 6/2006 | Rosenman et al. |
| 2006/0135993 A1 | 6/2006 | Seguin |
| 2006/0184198 A1 | 8/2006 | Bales et al. |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Rahdert et al. |
| 2006/0276890 A1 | 12/2006 | Solem et al. |
| 2007/0016225 A1 | 1/2007 | Nakao |
| 2007/0038293 A1 | 2/2007 | St et al. |
| 2007/0060997 A1 | 3/2007 | de Boer |
| 2007/0073185 A1 | 3/2007 | Nakao |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0173757 A1 | 7/2007 | Levine et al. |
| 2007/0197858 A1 | 8/2007 | Goldfarb et al. |
| 2007/0198082 A1 | 8/2007 | Kapadia et al. |
| 2007/0260225 A1 | 11/2007 | Sakakine et al. |
| 2007/0287884 A1 | 12/2007 | Schena |
| 2008/0009858 A1 | 1/2008 | Rizvi |

(56) References Cited

U.S. PATENT DOCUMENTS

| | | |
|---|---|---|
| 2008/0039935 A1 | 2/2008 | Buch et al. |
| 2008/0045936 A1 | 2/2008 | Vaska et al. |
| 2008/0051703 A1 | 2/2008 | Thornton et al. |
| 2008/0051807 A1 | 2/2008 | St et al. |
| 2008/0097467 A1 | 4/2008 | Gruber et al. |
| 2008/0097489 A1 | 4/2008 | Goldfarb et al. |
| 2008/0167714 A1 | 7/2008 | St et al. |
| 2008/0183194 A1 | 7/2008 | Goldfarb et al. |
| 2008/0188850 A1 | 8/2008 | Mody et al. |
| 2008/0195126 A1 | 8/2008 | Solem |
| 2008/0243249 A1 | 10/2008 | Kohm et al. |
| 2008/0294175 A1 | 11/2008 | Bardsley et al. |
| 2008/0312496 A1 | 12/2008 | Zwolinski |
| 2009/0012538 A1 | 1/2009 | Saliman et al. |
| 2009/0036768 A1 | 2/2009 | Seehusen et al. |
| 2009/0156995 A1 | 6/2009 | Martin et al. |
| 2009/0163934 A1 | 6/2009 | Raschdorf et al. |
| 2009/0177266 A1 | 7/2009 | Powell et al. |
| 2009/0192510 A1 | 7/2009 | Bahney |
| 2009/0198322 A1 | 8/2009 | Deem et al. |
| 2009/0204005 A1 | 8/2009 | Keast et al. |
| 2009/0209955 A1 | 8/2009 | Forster et al. |
| 2009/0209991 A1 | 8/2009 | Hinchliffe et al. |
| 2009/0270858 A1 | 10/2009 | Hauck et al. |
| 2009/0276039 A1 | 11/2009 | Meretei |
| 2009/0281619 A1 | 11/2009 | Le et al. |
| 2009/0326567 A1 | 12/2009 | Goldfarb et al. |
| 2010/0016958 A1 | 1/2010 | St et al. |
| 2010/0022823 A1 | 1/2010 | Goldfarb et al. |
| 2010/0044410 A1 | 2/2010 | Argentine et al. |
| 2010/0121437 A1 | 5/2010 | Subramanian et al. |
| 2010/0152612 A1 | 6/2010 | Headley et al. |
| 2010/0217261 A1 | 8/2010 | Watson |
| 2010/0262231 A1 | 10/2010 | Tuval et al. |
| 2010/0268226 A1 | 10/2010 | Epp et al. |
| 2010/0298929 A1 | 11/2010 | Thornton et al. |
| 2011/0009864 A1 | 1/2011 | Bucciaglia et al. |
| 2011/0184405 A1 | 7/2011 | Mueller |
| 2011/0224710 A1 | 9/2011 | Bleich |
| 2011/0238052 A1 | 9/2011 | Robinson |
| 2011/0282250 A1 | 11/2011 | Fung et al. |
| 2012/0022527 A1 | 1/2012 | Woodruff et al. |
| 2012/0022640 A1 | 1/2012 | Gross et al. |
| 2012/0065464 A1 | 3/2012 | Ellis et al. |
| 2012/0150194 A1 | 6/2012 | Odermatt et al. |
| 2012/0157765 A1 | 6/2012 | Mitelberg |
| 2012/0172915 A1 | 7/2012 | Fifer et al. |
| 2012/0179184 A1 | 7/2012 | Orlov |
| 2012/0265222 A1 | 10/2012 | Gordin et al. |
| 2012/0310330 A1 | 12/2012 | Buchbinder et al. |
| 2012/0316639 A1 | 12/2012 | Kleinschrodt |
| 2012/0330348 A1 | 12/2012 | Strauss et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0109910 A1 | 5/2013 | Alexander et al. |
| 2013/0172828 A1 | 7/2013 | Kappel et al. |
| 2013/0317515 A1 | 11/2013 | Kuroda et al. |
| 2014/0039511 A1 | 2/2014 | Morris et al. |
| 2014/0135799 A1 | 5/2014 | Henderson |
| 2014/0228871 A1 | 8/2014 | Cohen et al. |
| 2014/0276913 A1* | 9/2014 | Tah ............... A61B 17/221 606/114 |
| 2014/0309670 A1 | 10/2014 | Bakos et al. |
| 2014/0324164 A1 | 10/2014 | Gross et al. |
| 2014/0350662 A1 | 11/2014 | Vaturi |
| 2014/0358224 A1 | 12/2014 | Tegels et al. |
| 2014/0364866 A1 | 12/2014 | Dryden et al. |
| 2014/0379074 A1 | 12/2014 | Spence et al. |
| 2015/0005704 A1 | 1/2015 | Heisel et al. |
| 2015/0005801 A1 | 1/2015 | Marquis et al. |
| 2015/0051698 A1 | 2/2015 | Ruyra et al. |
| 2015/0094800 A1 | 4/2015 | Chawla |
| 2015/0112430 A1 | 4/2015 | Creaven et al. |
| 2015/0211946 A1 | 7/2015 | Pons et al. |
| 2015/0230947 A1 | 8/2015 | Krieger et al. |
| 2015/0257877 A1 | 9/2015 | Hernandez |
| 2015/0257883 A1 | 9/2015 | Basude et al. |
| 2015/0306806 A1 | 10/2015 | Dando et al. |
| 2015/0313581 A1 | 11/2015 | Wolfe et al. |
| 2016/0015410 A1 | 1/2016 | Asirvatham et al. |
| 2016/0074165 A1 | 3/2016 | Spence et al. |
| 2016/0174979 A1 | 6/2016 | Wei |
| 2016/0317174 A1 | 11/2016 | Dake |
| 2017/0042678 A1 | 2/2017 | Ganesan et al. |
| 2017/0100183 A1 | 4/2017 | Iaizzo et al. |
| 2017/0143330 A1 | 5/2017 | Basude et al. |
| 2017/0202559 A1 | 7/2017 | Taha |
| 2017/0232238 A1 | 8/2017 | Biller et al. |
| 2018/0008268 A1 | 1/2018 | Khairkhahan |
| 2018/0028215 A1 | 2/2018 | Cohen |
| 2018/0092661 A1* | 4/2018 | Prabhu ........... A61B 17/320783 |
| 2018/0133010 A1 | 5/2018 | Kizuka |
| 2018/0161159 A1 | 6/2018 | Lee et al. |
| 2018/0360457 A1 | 12/2018 | Ellis et al. |
| 2019/0029790 A1 | 1/2019 | Bak-Boychuk et al. |
| 2019/0183571 A1 | 6/2019 | De Marchena |
| 2019/0298517 A1 | 10/2019 | Sanchez et al. |
| 2019/0307458 A1 | 10/2019 | Mathis et al. |
| 2020/0121460 A1 | 4/2020 | Dale et al. |
| 2021/0113232 A1 | 4/2021 | Ortiz et al. |
| 2021/0145574 A1* | 5/2021 | Childs ................... A61F 2/2427 |

FOREIGN PATENT DOCUMENTS

| | | |
|---|---|---|
| CN | 103841899 A | 6/2014 |
| CN | 104244841 A | 12/2014 |
| DE | 3504292 C1 | 7/1986 |
| DE | 9100873 U1 | 4/1991 |
| DE | 10116168 A1 | 11/2001 |
| EP | 0179562 A1 | 4/1986 |
| EP | 0558031 A2 | 9/1993 |
| EP | 0684012 A2 | 11/1995 |
| EP | 0727239 A2 | 8/1996 |
| EP | 0782836 A1 | 7/1997 |
| EP | 1230899 A1 | 8/2002 |
| EP | 1674040 A2 | 6/2006 |
| EP | 1980288 A1 | 10/2008 |
| EP | 2005912 A2 | 12/2008 |
| EP | 2537487 A1 | 12/2012 |
| EP | 2641570 A1 | 9/2013 |
| EP | 2702965 A1 | 3/2014 |
| EP | 2740419 A1 | 6/2014 |
| EP | 3009103 A1 | 4/2016 |
| FR | 2705556 A1 | 12/1994 |
| FR | 2768324 A1 | 3/1999 |
| FR | 2903292 A1 | 1/2008 |
| GB | 1598111 A | 9/1981 |
| GB | 2151142 A | 7/1985 |
| JP | 09-253030 A | 9/1997 |
| JP | 11-089937 A | 4/1999 |
| JP | 2000-283130 A | 10/2000 |
| JP | 2001-517529 A | 10/2001 |
| JP | 2006-528911 A | 12/2006 |
| JP | 2013-516244 A | 5/2013 |
| JP | 2013-523384 A | 6/2013 |
| JP | 2014-523274 A | 9/2014 |
| JP | 2015-502548 A | 1/2015 |
| JP | 2018-030008 A | 3/2018 |
| WO | 81/00668 A1 | 3/1981 |
| WO | 91/01689 A1 | 2/1991 |
| WO | 91/18881 A1 | 12/1991 |
| WO | 92/12690 A1 | 8/1992 |
| WO | 94/18881 A1 | 9/1994 |
| WO | 94/18893 A1 | 9/1994 |
| WO | 95/08292 A1 | 3/1995 |
| WO | 95/11620 A2 | 5/1995 |
| WO | 95/15715 A1 | 6/1995 |
| WO | 96/14032 A1 | 5/1996 |
| WO | 96/20655 A1 | 7/1996 |
| WO | 96/22735 A1 | 8/1996 |
| WO | 96/30072 A1 | 10/1996 |
| WO | 97/18746 A2 | 5/1997 |
| WO | 97/25927 A1 | 7/1997 |

(56) References Cited

FOREIGN PATENT DOCUMENTS

| | | |
|---|---|---|
| WO | 97/26034 A1 | 7/1997 |
| WO | 97/38748 A2 | 10/1997 |
| WO | 97/39688 A2 | 10/1997 |
| WO | 97/48436 A2 | 12/1997 |
| WO | 98/07375 A1 | 2/1998 |
| WO | 98/24372 A1 | 6/1998 |
| WO | 98/30153 A1 | 7/1998 |
| WO | 98/32382 A1 | 7/1998 |
| WO | 98/35638 A1 | 8/1998 |
| WO | 99/00059 A1 | 1/1999 |
| WO | 99/01377 A1 | 1/1999 |
| WO | 99/07295 A1 | 2/1999 |
| WO | 99/07354 A2 | 2/1999 |
| WO | 99/13777 A1 | 3/1999 |
| WO | 99/44524 A2 | 9/1999 |
| WO | 99/66967 A1 | 12/1999 |
| WO | 00/02489 A1 | 1/2000 |
| WO | 00/03651 A1 | 1/2000 |
| WO | 00/03759 A2 | 1/2000 |
| WO | 00/12168 A1 | 3/2000 |
| WO | 00/44313 A1 | 8/2000 |
| WO | 00/59382 A1 | 10/2000 |
| WO | 00/60995 A2 | 10/2000 |
| WO | 01/00111 A1 | 1/2001 |
| WO | 01/00114 A1 | 1/2001 |
| WO | 01/03651 A2 | 1/2001 |
| WO | 01/26557 A1 | 4/2001 |
| WO | 01/26586 A1 | 4/2001 |
| WO | 01/26587 A1 | 4/2001 |
| WO | 01/26588 A2 | 4/2001 |
| WO | 01/26703 A1 | 4/2001 |
| WO | 01/28432 A1 | 4/2001 |
| WO | 01/28455 A1 | 4/2001 |
| WO | 01/47438 A1 | 7/2001 |
| WO | 01/49213 A2 | 7/2001 |
| WO | 01/50985 A1 | 7/2001 |
| WO | 01/54618 A1 | 8/2001 |
| WO | 01/56512 A1 | 8/2001 |
| WO | 01/66001 A2 | 9/2001 |
| WO | 01/70320 A1 | 9/2001 |
| WO | 01/89440 A2 | 11/2001 |
| WO | 01/95831 A2 | 12/2001 |
| WO | 01/95832 A2 | 12/2001 |
| WO | 01/97741 A2 | 12/2001 |
| WO | 02/00099 A2 | 1/2002 |
| WO | 02/01999 A2 | 1/2002 |
| WO | 02/03892 A1 | 1/2002 |
| WO | 02/34167 A2 | 5/2002 |
| WO | 02/60352 | 8/2002 |
| WO | 02/62263 | 8/2002 |
| WO | 02/62270 | 8/2002 |
| WO | 02/62408 | 8/2002 |
| WO | 03/01893 A2 | 1/2003 |
| WO | 03/03930 | 1/2003 |
| WO | 03/20179 | 3/2003 |
| WO | 03/28558 A2 | 4/2003 |
| WO | 03/37171 | 5/2003 |
| WO | 03/47467 | 6/2003 |
| WO | 03/49619 | 6/2003 |
| WO | 03/73910 | 9/2003 |
| WO | 03/73913 | 9/2003 |
| WO | 03/82129 | 10/2003 |
| WO | 2003/105667 | 12/2003 |
| WO | 2004/004607 A1 | 1/2004 |
| WO | 2004/006810 A1 | 1/2004 |
| WO | 2004/012583 A2 | 2/2004 |
| WO | 2004/012789 A2 | 2/2004 |
| WO | 2004/014282 A2 | 2/2004 |
| WO | 2004/019811 A2 | 3/2004 |
| WO | 2004/030570 A2 | 4/2004 |
| WO | 2004/037317 A2 | 5/2004 |
| WO | 2004/045370 A2 | 6/2004 |
| WO | 2004/045378 A2 | 6/2004 |
| WO | 2004/045463 A2 | 6/2004 |
| WO | 2004/047679 A1 | 6/2004 |
| WO | 2004/062725 A1 | 7/2004 |
| WO | 2004/082523 A2 | 9/2004 |
| WO | 2004/082538 A2 | 9/2004 |
| WO | 2004/093730 A2 | 11/2004 |
| WO | 2004/103162 A2 | 12/2004 |
| WO | 2004/112585 A2 | 12/2004 |
| WO | 2004/112651 A2 | 12/2004 |
| WO | 2005/002424 A2 | 1/2005 |
| WO | 2005/018507 A2 | 3/2005 |
| WO | 2005/027797 A1 | 3/2005 |
| WO | 2005/032421 A2 | 4/2005 |
| WO | 2005/062931 A2 | 7/2005 |
| WO | 2005/112792 A2 | 12/2005 |
| WO | 2006/037073 A2 | 4/2006 |
| WO | 2006/105008 A1 | 10/2006 |
| WO | 2006/105009 A1 | 10/2006 |
| WO | 2006/113906 A1 | 10/2006 |
| WO | 2006/115875 A2 | 11/2006 |
| WO | 2006/115876 A2 | 11/2006 |
| WO | 2007/136829 A1 | 11/2007 |
| WO | 2008/103722 A2 | 8/2008 |
| WO | 2010/024801 A1 | 3/2010 |
| WO | 2010/121076 A2 | 10/2010 |
| WO | 2012/020521 A1 | 2/2012 |
| WO | 2013/049734 A1 | 4/2013 |
| WO | 2013/103934 A1 | 7/2013 |
| WO | 2014/064694 A2 | 5/2014 |
| WO | 2014/121280 A2 | 8/2014 |
| WO | 2016/022797 A1 | 2/2016 |
| WO | 2016/144708 A1 | 9/2016 |
| WO | 2016/150806 A1 | 9/2016 |
| WO | 2017/223073 A1 | 12/2017 |
| WO | 2018/009718 A1 | 1/2018 |
| WO | 2018/106482 A1 | 6/2018 |
| WO | 2018/236766 A1 | 12/2018 |
| WO | 2019/040943 A1 | 2/2019 |
| WO | 2019/195336 A1 | 10/2019 |

OTHER PUBLICATIONS

Park et al, Clinical Use of Blade Atrial Septostomy, Circulation, 1978, pp. 600-608, vol. 58.

Patel et al., #57 Epicardial Atrial Defibrillation: Novel Treatment of Postoperative Atrial Fibrillation, 2003 STS Presentation, [Abstract Only].

Privitera et al., "Alfieri Mitral Valve Repair: Clinical Outcome and Pathology," Circulation, 106:e173-e174 (2002).

Redaelli et al., "A Computational Study of the Hemodynamics After 'Edge-To-Edge' Mitral Valve Repair," Journal of Biomechanical Engineering, 123:565-570 (2001).

Reul et al., "Mitral Valve Reconstruction for Mitral Insufficiency," Progress in Cardiovascular Diseases, XXXIX(6):567-599 (1997).

Ricchi et al, Linear Segmental Annuloplasty for Mitral Valve Repair, Ann. Thorac. Surg., Jan. 7, 1997, pp. 1805-1806, vol. 63.

Robicsek et al., #60 The Bicuspid Aortic Valve: How Does It Function? Why Does It Fail? 2003 STS Presentation, [Abstract Only].

Rose et al., "Late MitraClip Failure: Removal Technique for Leaflet-Sparing Mitral Valve Repair", Journal of Cardiac Surgery, (Jul. 4, 2012), XP055047339, DOI: 10.1111/j. 1540-8191.2012.01483.x [retrieved on Dec. 11, 2012].

Supplemental European Search Report of EP Application No. 02746781, dated May 13, 2008, 3 pages total.

Supplementary European Search Report issued in European Application No. 05753261.6 dated Jun. 9, 2011, 3 pages total.

Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.

Takizawa H et al: Development of a microfine active bending catheter equipped with MIF tactile sensors", Micro Electro Mechanical Systems, 1999. MEMS '99. Twelfth IEEE Interna Tional Conference on Orlando, FL, USA Jan. 17-21, 1999, Piscataway, NJ,

(56) References Cited

OTHER PUBLICATIONS

USA, IEEE, US, Jan. 17, 1999 (Jan. 17, 1999), pp. 412-417, XP010321677, ISBN: 978-0-7803-5194-3 figures 1-3."

Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).

Tibayan et al., #59 Annular Geometric Remodeling in Chronic Ischemic Mitral Regurgitation, 2003 STS Presentation, [Abstract Only].

Timek et al., "Edge-to-edge mitral repair: gradients and three-dimensional annular dynamics in vivo during inotropic stimulation," Eur J. of Cardiothoracic Surg., 19:431-437 (2001).

Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).

Totaro, "Mitral valve repair for isolated prolapse of the anterior leaflet: an 11-year follow-up," European Journal of Cardio-thoracic Surgery, 15:119-126 (1999).

U.S. Provisional Application Filed on Jul. 6, 2016, by Khairkhahan., U.S. Appl. No. 62/359,121.

U.S. Provisional Application Filed on Nov. 7, 2016, by Khairkhahan., U.S. Appl. No. 62/418,571.

U.S. Provisional Application Filed on Oct. 22, 2018, by Dale et al., U.S. Appl. No. 62/748,947.

Uchida et al, Percutaneous Cardiomyotomy and Valvulotomy with Angioscopic Guidance, Am. Heart J., Apr. 1991, pp. 1221-1224, vol. 121.

Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.

Umana et al., "'Bow-tie' Mitral Valve Repair Successfully Addresses Subvalvular Dysfunction in Ischemic Mitral Regurgitation," Surgical Forum, XLVIII:279-280 (1997).

U.S. Appl. No. 14/216,813, filed Mar. 17, 2014, Hernandez.

Votta et al., "3-D Computational Analysis of the Stress Distribution on the Leaflets after Edge-to-Edge Repair of Mitral Regurgitation," Journal of Heart Valve Disease, 11:810-822 (2002).

Abe et al, "De Vega's Annuloplasty for Acquired Tricuspid Disease: Early and Late Results in 110 Patients", Ann. Thorac. Surg., pp. 670-676, vol. 48 (Jan. 1989).

Abe et al., "Updated in 1996—De Vega's Annuloplasty for Acquired Tricuspid Disease: Early and Late Results in 110 Patients", Ann. Thorac. Surg., pp. 1876-1877, vol. 62 (1996).

Agricola et al., "Mitral Valve Reserve in Double Orifice Technique: an Exercise Echocardiographic Study," Journal of Heart Valve Disease, 11(5):637-643 (2002).

Alfieri et al., "An Effective Technique to Correct Anterior Mitral Leaflet Prolapse," J. Card Surg., 14:468-470 (1999).

Alfieri et al., "Novel Suture Device for Beating Heart Mitral Leaflet Approximation," Annals of Thoracic Surgery, 74:1488-1493 (2002).

Alfieri et al., "The double orifice technique in mitral valve repair: a simple solution for complex problems," Journal of Thoracic and Cardiovascular Surgery, 122:674-681 (2001).

Alfieri et al., "The Edge to Edge Technique," The European Association For Cardio-Thoracic Surgery, 14th Annual Meeting, Frankfurt/ Germany, Oct. 7-11, 2000, Post Graduate Courses, Book of Proceedings.

Alfieri, "The Edge-to-Edge Repair of the Mitral Valve," [Abstract] 6th Annual New Era Cardiac Care: Innovation & Technology, Heart Surgery Forum, (Jan. 2003) pp. 103.

Ali Khan et al, Blade Atrial Septostomy: Experience with the First 50 Procedures, Cathet. Cardiovasc. Diagn., Aug. 1991, pp. 257-262, vol. 23.

Alvarez et al, Repairing the Degenerative Mitral Valve: Ten to Fifteen-year Follow-up, Journal Thoracic of Cardiovascular Surgery, Aug. 1996, pp. 238-247, vol. 112, No. 2.

Arisi et al., "Mitral Valve Repair with Alfieri Technique in Mitral Regurgitation of Diverse Etiology: Early Echocardiographic Results," Circulation Supplement II, 104(17):3240 (2001).

Bach et al, Early Improvement in Congestive Heart Failure After Correction of Secondary Mitral Regurgitation in End-stage Cardiomyopathy, American Heart Journal, Jun. 1995, pp. 1165-1170, vol. 129, No. 6.

Bach et al, Improvement Following Correction of Secondary Mitral Regurgitation in End-stage Cardiomyopathy With Mitral Annuloplasty, Am. J. Cardiol., Oct. 15, 1996, pp. 966-969, vol. 78.

Bailey, "Mitral Regurgitation" in Surgery of the Heart, Chapter 20, pp. 686-737 (1955).

Bernal et al., "The Valve Racket: a new and different concept of atrioventricular valve repair," Eur. J. Cardio-thoracic Surgery 29:1026-1029 (2006).

Bhudia et al., "Edge-to-Edge (Alfieri) Mitral Repair: Results in Diverse Clinical Settings," Ann Thorac Surg, 77:1598-1606 (2004).

Bhudia, #58 Edge-to-edge mitral repair: a versatile mitral repair technique, 2003 STS Presentation, [Abstract Only], 2004.

Bolling et al, Surgery for Acquired Heart Disease: Early Outcome of Mitral Valve Reconstruction in Patients with End-stage Cardiomyopathy, Journal of Thoracic and Cariovascular Surgery, Apr. 1995, pp. 676-683, vol. 109, No. 4.

Borghetti et al., "Preliminary observations on haemodynamics during physiological stress conditions following 'double-orifice' mitral valve repair," European Journal of Cardio-thoracic Surgery, 20:262-269 (2001).

Castedo, "Edge-to-Edge Tricuspid Repair for Redeveloped Valve Incompetence after DeVega's Annuloplasty," Ann Thora Surg., 75:605-606 (2003).

Chinese Office Action issued in Chinese Application No. 200980158707.2 dated Sep. 9, 2013.

Communication dated Apr. 16, 2018 from the European Patent Office in counterpart European application No. 04752603.3.

Communication dated Apr. 28, 2017 issued by the European Patent Office in counterpart application No. 16196023.2.

Communication dated Jan. 26, 2017, from the European Patent Office in counterpart European application No. 16196023.2.

Communication dated May 8, 2017, from the European Patent Office in counterpart European Application No. 04752714.8.

Dang N C et al., "Surgical Revision After Percutaneous Mitral Valve Repair with a Clip: Initial Multicenter Experience", The Annals of Thracic Surgery, Elsevier, United States, vol. 80, No. 6, pp. 2338-2342, (Dec. 1, 2005), XP027732951, ISSN:0003-4975 [retrieved on Dec. 1, 2005].

Dec et al, Idiopathic Dilated Cardiomyopathy, The New England Journal of Medicine, Dec. 8, 1994, pp. 1564-1575, vol. 331, No. 23.

Dottori et al., "Echocardiographic imaging of the Alfieri type mitral valve repair," Ital. Heart J., 2(4):319-320 (2001).

Downing et al., "Beating heart mitral valve surgery: Preliminary model and methodology," Journal of Thoracic and Cardiovascular Surgery, 123(6):1141-1146 (2002).

Extended European Search Report, dated Oct. 17, 2014, issued in European Patent Application No. 06751584.1.

Falk et al., "Computer-Enhanced Mitral Valve Surgery: Toward a Total Endoscopic Procedure," Seminars in Thoracic and Cardiovascular Surgery, 11(3):244-249 (1999).

Feldman, et al. Randomized Comparison of Percutaneous Repair and Surgery for Mitral Regurgitation: 5-Year Results of Everest Ii. J Am Coll Cardiol. Dec. 29, 2015;66(25):2844-2854.

Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).

Frazier et al., #62 Early Clinical Experience with an Implantable, Intracardiac Circulatory Support Device: Operative Considerations and Physiologic Implications, 2003 STS Presentation, 1 page total. [Abstract Only].

Fucci et al, Improved Results with Mitral Valve Repair Using New Surgical Techniques, Eur. J. Cardiothorac. Surg., Nov. 1995, pp. 621-627, vol. 9.

Fundaro et al., "Chordal Plication and Free Edge Remodeling for Mitral Anterior Leaflet Prolapse Repair: 8-Year Follow-up," Annals of Thoracic Surgery, 72:1515-1519 (2001).

(56) References Cited

OTHER PUBLICATIONS

Garcia-Rinaldi et al., "Left Ventricular vol. Reduction and Reconstruction is Ischemic Cardiomyopathy," Journal of Cardiac Surgery, 14:199-210 (1999).
Gateliene, "Early and postoperative results results of metal and tricuspid valve insufficiency surgical treatment using edge-to-edge central coaptation procedure," (Oct. 2002) 38 (Suppl 2):172 175.
Gatti et al., "The edge to edge technique as a trick to rescue an imperfect mitral valve repair," Eur. J. Cardiothorac Surg, 22:817-820 (2002).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
Izzat et al., "Early Experience with Partial Left Ventriculectomy in the Asia-Pacific Region," Annals of Thoracic Surgery, 67:1703-1707 (1999).
Kallner et al., "Transaortic Approach for the Alfieri Stitch," Ann Thorac Surg, 71:378-380 (2001).
Kameda et al., Annuloplasty for Severe Mitral Regurgitation Due to Dilated Cardiomyopathy, Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Khan et al., "Blade Atrial Septostomy; Experience with the First 50 Procedures", Catheterization and Cardiovascular Diagnosis, 23:257-262 (1991).
Kherani et al., "The Edge-To-Edge Mitral Valve Repair: The Columbia Presbyterian Experience," Ann. Thorac. Surg., 78:73-76 (2004).
Kron et al., "Surgical Relocation of the Posterior Papillary Muscle in Chronic Ischemic Mitral Regurgitation," Annals. Of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "The double-orifice technique for mitral valve reconstruction: predictors of postoperative outcome," Eur J. Cardiothorac Surg, 20:583-589 (2001).
Maisano et al., The Edge-to-edge Technique: A Simplified Method to Correct Mitral Insufficiency, Eur. J. Cardiothorac. Surg., Jan. 14, 1998, pp. 240-246, vol. 13.
Maisano et al, The future of transcatheter mitral valve interventions: competitive or complementary role of repair vs. replacement? Eur Heart J. Jul. 7, 2015; 36(26):1651-1659.
Maisano et al., "The double orifice repair for Barlow Disease: a simple solution for a complex repair," Supplement I Circulation, (Nov. 1999); 100(18):1-94.
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The Future of Transcatheter Mitral Valve Interventions: Competitive or Complementary Role of Repair vs. Replacement?", Eur Heart J.36(26):1651-1659 ( Jul. 7, 2015 ).
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, (1996) 10:867-873.
Mantovani et al., "Edge-to-edge Repair of Congenital Familiar Tricuspid Regurgitation: Case Report," J. Heart Valve Dis., 9:641-643 (2000).
McCarthy et al, "Tricuspid Valve Repair With the Cosgrove-Edwards Annuloplasty System", Ann. Thorac. Surg., 64:267-8 ( Jan. 16, 1997).
McCarthy et al., "Partial left ventriculectomy and mitral valve repair for end-stage congestive heart failure," European Journal of Cardio-thoracic Surgery, 13:337-343 (1998).
McCarthy et al., "Tricuspid Valve Repair With the Cosgrove-Edwards Annuloplasty System", Ann. Throac Surg. 64:267-8 (Jan. 16, 1997).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. 1):1-29-1-35 (2001).
Noera et al., "Tricuspid Valve Incompetence Caused by Nonpenetrating Thoracic Trauma", Annals of Thoracic Surgery, 51:320-322 (1991).
Notice of Allowance received for U.S. Appl. No. 14/216,787, filed Nov. 7, 2016.
Notice of Allowance received for U.S. Appl. No. 14/216,787, mailed on Nov. 7, 2016.
Notice of Allowance received for U.S. Appl. No. 14/577,852, filed Apr. 25, 2018.
Notice of Allowance received for U.S. Appl. No. 14/577,852, mailed on Apr. 25, 2018.
Notice of Allowance received for U.S. Appl. No. 15/642,245, mailed on Jan. 29, 2020.
Notice of Allowance received for U.S. Appl. No. 15/642,245, mailed on Mar. 27, 2020.
Notice of Allowance received for U.S. Appl. No. 15/642,245, mailed on Nov. 6, 2019.
Notice of Allowance received for U.S. Appl. No. 15/423,060, mailed on Jan. 27, 2020.
Office Action received for U.S. Appl. No. 14/216,787, filed Apr. 8, 2016.
Office Action received for U.S. Appl. No. 14/216,787, mailed on Apr. 8, 2016.
Office Action received for U.S. Appl. No. 14/216,813, filed Apr. 6, 2018.
Office Action received for U.S. Appl. No. 14/216,813, filed Dec. 15, 2017.
Office Action received for U.S. Appl. No. 14/216,813, filed Mar. 9, 2017.
Office Action received for U.S. Appl. No. 14/216,813, mailed on Apr. 6, 2018.
Office Action received for U.S. Appl. No. 14/216,813, mailed on Dec. 15, 2017.
Office Action received for U.S. Appl. No. 14/216,813, mailed on Mar. 9, 2017.
Office Action received for U.S. Appl. No. 14/577,852, filed May 16, 2017.
Office Action received for U.S. Appl. No. 14/577,852, filed Oct. 20, 2016.
Office Action received for U.S. Appl. No. 14/577,852, filed Sep. 7, 2017.
Office Action received for U.S. Appl. No. 14/577,852, mailed on May 16, 2017.
Office Action received for U.S. Appl. No. 14/577,852, mailed on Oct. 20, 2016.
Office Action received for U.S. Appl. No. 14/577,852, mailed on Sep. 7, 2017.

(56) References Cited

OTHER PUBLICATIONS

Office Action received for U.S. Appl. No. 15/423,060, mailed on Apr. 25, 2019.
Office Action received for U.S. Appl. No. 15/423,060, mailed on Aug. 19, 2019.
Office Action received for U.S. Appl. No. 15/423,060, mailed on Oct. 28, 2019.
Office Action received for U.S. Appl. No. 15/642,245, mailed on Aug. 9, 2019.
Office Action received for U.S. Appl. No. 15/724,545, filed Dec. 27, 2019.
Office Action received for U.S. Appl. No. 15/724,545, mailed on Dec. 27, 2019.
Office Action received for U.S. Appl. No. 15/724,545, mailed on May 1, 2020.
Osawa et al., "Partial Left Ventriculectomy in a 3-Year Old Boy with Dilated Cardiomyopathy," Japanese Journal of Thoracic and Cardiovascular Surg, 48:590-593 (2000).

\* cited by examiner

DEVICES AND METHODS FOR CLIP SEPARATION

CROSS-REFERENCE TO RELATED APPLICATIONS

This application claims priority to U.S. Provisional Patent Application No. 63/020,671, filed May 6, 2020, the entire contents of which are incorporated by reference herein.

BACKGROUND OF THE INVENTION

The mitral valve controls blood flow from the left atrium to the left ventricle of the heart, preventing blood from flowing backwards from the left ventricle into the left atrium so that it is instead forced through the aortic valve for delivery of oxygenated blood throughout the body. A properly functioning mitral valve opens and closes to enable blood flow in one direction. However, in some circumstances the mitral valve is unable to close properly, allowing blood to regurgitate back into the atrium.

Mitral valve regurgitation has several causes. Functional mitral valve regurgitation is characterized by structurally normal mitral valve leaflets that are nevertheless unable to properly coapt with one another to close properly due to other structural deformations of surrounding heart structures. Other causes of mitral valve regurgitation are related to defects of the mitral valve leaflets, mitral valve annulus, or other mitral valve tissues.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bowtie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity. In some patients, a fixation device can be installed into the heart using minimally invasive techniques. The fixation device can hold the adjacent segments of the opposed valve leaflets together and may reduce mitral valve regurgitation. One such device used to clip the anterior and posterior leaflets of the mitral valve together is the MitraClip® fixation device, sold by Abbott Vascular, Santa Clara, California, USA.

However, sometimes after a fixation device is installed, undesirable mitral valve regurgitation can still exist, or can arise again. For these sub-optimally treated patients, the presence of a fixation device in their mitral valves obstructs transcatheter mitral valve replacement. These patients may also be considered too frail to tolerate open-heart surgery, so they are left with no viable options to further improve the function of their mitral valve.

Accordingly, it would be desirable to provide alternative and additional methods, devices, and systems for removing or disabling fixation devices that are already installed. The methods, devices, and systems may be useful for repair of tissues in the body other than heart valves. At least some of these objectives will be met by the inventions described hereinbelow.

BRIEF SUMMARY OF THE INVENTION

Implementations of the present invention solve one or more problems in the art with systems, methods, and apparatus configured to cut leaflet tissue at a cardiac valve. A device may comprise a guide catheter having a proximal end and a distal end, the guide catheter being positionable at a cardiac valve. The device may further include a cutting mechanism routable through the guide catheter and configured to extend from the distal end of the guide catheter, the cutting mechanism configured to cut a portion of leaflet tissue of the cardiac valve. Finally, the device may comprise a handle coupled to the proximal end of the guide catheter, the handle comprising at least one control operatively connected to the cutting mechanism such that the at least one control is configured to provide selective actuation of the cutting mechanism.

A system for cutting leaflet tissue at a cardiac valve may comprise a guide catheter having a proximal end and a distal end, wherein the distal end of the guide catheter is guided to a position at a cardiac valve. The system may also comprise a cutting mechanism having a proximal end and a distal end, wherein the cutting mechanism is routable through the guide catheter and configured to extend beyond the distal end of the guide catheter and retract into the guide catheter, wherein the cutting mechanism is configured to cut a portion of leaflet tissue of the cardiac valve.

A method of cutting cardiac valve tissue at a cardiac valve within a body may comprise positioning a guide catheter, having a proximal and a distal end such that the distal end of the guide catheter is positioned at a cardiac valve. The method may also include routing a cutting mechanism through the guide catheter such that the cutting mechanism extends distally beyond the distal end of the guide catheter, wherein the cardiac valve is associated with an interventional implant that approximates adjacent leaflets of the cardiac valve, and a cutting mechanism extends from the guide catheter. Finally, the method may comprise actuating the cutting mechanism to cut at a portion of least one leaflet of the approximated adjacent leaflet.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Implementations of the present invention solve one or more problems in the art with systems, methods, and apparatus configured to cut leaflet tissue at a cardiac valve. More specifically, in at least one embodiment of the present invention a device may comprise a guide catheter having a proximal end and a distal end, the guide catheter being positionable at a cardiac valve. The device may further include a cutting mechanism routable through the guide catheter and configured to extend from the distal end of the guide catheter, the cutting mechanism configured to cut a portion of leaflet tissue of the cardiac valve. Finally, the device may comprise a handle coupled to the proximal end of the guide catheter, the handle comprising at least one control operatively connected to the cutting mechanism such that the at least one control is configured to provide selective actuation of the cutting mechanism.

Figure 1:
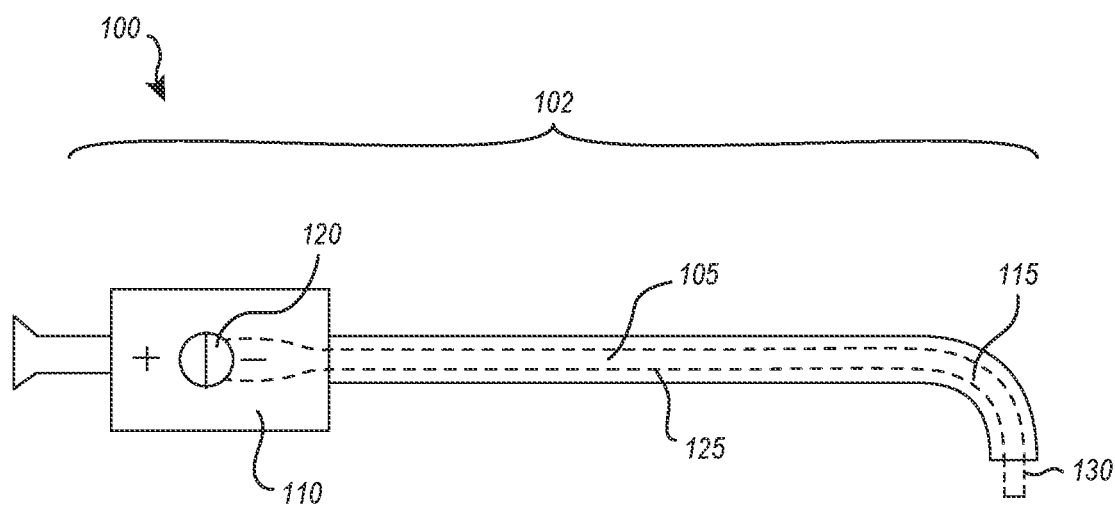
FIG. 1 illustrates an exemplary delivery system that may be utilized for guiding and/or delivering a cutting mechanism to a cardiac valve.

FIG. 1 illustrates an exemplary embodiment of a leaflet cutting system 100, which can include a delivery system 102 that may be utilized for guiding and/or delivering a cutting mechanism to the cardiac valve. In at least one embodiment, the delivery system 102 can include a guide catheter 105 having a proximal end and a distal end 115. The delivery system may comprise a handle 110 positioned on the proximal end of the guide catheter 105. The guide catheter 105 may be operatively coupled to the handle 110. The guide catheter 105 may be steerable to enable the guiding and orienting of the guide catheter 105, including the distal end 115 of the guide catheter 105. For example, the handle 110 may include at least one control 120 (e.g., a dial, a switch, a slider, a button, etc.) that can be actuated to control the movement and curvature of the distal end 115 of the guide catheter 105.

In at least one embodiment, the at least one control 120 is operatively coupled to one or more control lines 125 (e.g., pull wires) extending from the handle 110 through the guide catheter 105 to the distal end 115 of the guide catheter (e.g., through one or more lumens in the guide catheter 105). Actuation of the at least one control 120 may adjust the tensioning of a control line 125 to pull the guide catheter 105 in the corresponding direction. FIG. 1 shows the handle 110 as having a single control 120 for providing steerability. Alternatively, a handle 110 may comprise more than one control 120 associated with any number of control lines. In at least one embodiment, the at least one control 120 can adjust four or more control lines 125 to selectively control directional movement and/or curvature of the steerable portion 117 of the guide catheter 105.

While control lines or wires are described at various points in this application, it should be understood that references made throughout this application to control lines or wires may be a single wire or a plurality of wires including, or made of, steel, titanium alloy, aluminum alloy, nickel alloy, other metals, a shape memory material (such as a shape memory alloy or shape memory polymer), inorganic polymer, organic polymer, ceramic, carbon materials, or other flexible material with sufficient tensile strength. For example, a control line 125 may be a steel cable. In another example, a control line 125 may be a monofilament suture. In another example, a control line 125 may be a multifilament suture. In yet another example, a control line 125 may be a braided suture.

It is desirable for guide catheter 105 to provide an adjustable distal end 115, which is capable of being positioned within a target body cavity in a desired orientation. Guide catheter 105 should have a large lumen diameter to accommodate the passage of a variety of devices, such as the various embodiments of the cutting mechanisms discussed hereinafter and should have good wall strength to avoid kinking or collapse when bent around tight curves, and should have good column, tensile, and torsional strength to avoid deformation when the devices are passed through the lumen and torqued or translated. Guide catheter 105 should provide for a high degree of controlled deflection at its distal end 115 but should not take up significant lumen area to allow for passage of interventional devices, such as the cutting mechanisms discussed below. Further, guide catheter 105 should be positionable in a manner which allows compound curves to be formed, for example curvature within more than one plane. Such manipulation should also allow fine control over distal end 115 to accommodate anatomical variations within the same type of body cavity and for use in different types of body cavities.

The guide catheter 105 may comprise a main body made of or including a flexible material. The main body may be made of or include a variety of flexible materials, such as thermoplastic elastomers (TPE). In some embodiments, the main body may be a polyether block amide (PEBA or PEBAX). The main body may have a constant durometer or may have varying durometer that varies along its longitudinal length or that varies in different portions of the body. For example, the main body of guide catheter 105 may be made of or include a body material having a durometer of 25 D to 75 D. In another example, the main body of guide catheter 105 may be made of or include a body material that has a durometer of about 45 D. In at least one embodiment, the body material may include PEBAX 4533. In at least another embodiment, the body material may include PEBAX 3533.

The guide catheter 105 preferably defines a central lumen, extending axially through its entire length, through which other elongate elements, such as the cutting mechanisms may be inserted for accessing a treatment site. The central lumen may also include a central lumen lining on an inner surface thereof. In some embodiments, the central lumen lining may be a protective material that protects the interior walls from damage due to another element of the elongated member moving through or within the central lumen. In other embodiments, the central lumen lining may include a lubricious coating that reduces friction between the interior wall and another element of the elongated member moving through or within the central lumen. The central lumen lining may include PEBA or PEBAX, polytetrafluoroethylene ("PTFE"), polyetheretherketone ("PEEK"), other polymers, thermoplastic polyurethane ("TPU"), polyethylene with pebble stone surface, silicone oil stainless steel, Nitinol, other metals, or combinations thereof. In at least one embodiment, the central lumen lining may include a plurality of PEBA or PEBAX materials having different durometers.

In other embodiments, the guide catheter 105 may also have an outer layer. In some embodiments, the outer layer may be made of or include a single material or may be made of or include different materials to impart different handling characteristics to the guide catheter 105. For example, the outer layer may be made of or include softer materials to promote flexibility of the guide catheter 105. In other examples, the outer layer may be made of or include stiffer materials to promote pushability and/or torqueability of the guide catheter 105. In yet other examples, the outer layer may include lubricious materials to reduce friction between the guide catheter 105 and the body lumen of the patient. The outer layer may include PEBA or PEBAX, polytetrafluoroethylene ("PTFE"), polyetheretherketone ("PEEK"), other polymers, thermoplastic polyurethane ("TPU"), polyethylene with pebble stone surface, silicone oil stainless steel, Nitinol, other metals, or combinations thereof. In at least one embodiment, the outer layer may include a plurality of PEBA or PEBAX materials having different durometers.

In some embodiments, the outer layer of guide catheter 105 may also include a radiopaque marker to improve visualization of guide catheter 105 during a medical procedure. For example, the outer layer may include a barium sulfate (BaSO4), gold, platinum, platinum iridium, iodine, other radiopaque materials, or combinations thereof on a distal portion of guide catheter 105. In at least one embodiment, one or more additional radiopaque markers may be longitudinally located at one or more intermediate locations along the length of guide catheter 105.

The curves of guide catheter 105 may be formed by any suitable means. In some embodiments, one or more of the curves are preset so that the curve is formed by shape memory. For example, guide catheter 105 may be comprised of a flexible polymer material in which a curve is preset by heating. When guide catheter 105 is loaded on a guidewire, dilator, obturator or introductory device, the flexibility of guide catheter 105 can allow it to follow the shape or path of the introductory device for proper positioning within the body. When the introductory device is pulled back and/or removed, guide catheter 105 can then resume the shape memory configuration which was preset into the catheter.

Alternatively, the curves may be formed or enhanced with the use of one or more steering mechanisms. In some embodiments, the steering mechanism comprises at least one control wire or pullwire attached to one of the guide catheter 105, wherein actuation of the steering mechanism applies tension to the at least one pullwire whereby the curve is formed. The pullwires can extend through the central lumen or through individual lumens in the wall of guide catheter 105. It may be appreciated that more than one pullwire may extend through any given lumen. The presence of each pullwire allows curvature of guide catheter 105 in the direction of the pullwire. For example, when pulling or applying tension to a pullwire extending along one side of the catheter, the catheter will bend, arc or form a curvature toward that side. To then straighten the catheter, the tension may be relieved for recoiling effects or tension may be applied to a pullwire extending along the opposite side of the catheter. Therefore, pullwires are often symmetrically placed along the sides of the catheter.

Thus, in some embodiments at least two pullwires are attached in diametrically opposed locations wherein applying tension to one of the pullwires curves the catheter in one direction and applying tension to the pullwire attached in the diametrically opposed location curves the catheter in another direction opposite to the one direction. The diametrically opposed pullwires may be considered a set. Any number of sets may be present in a catheter to provide unlimited directions of curvature. In some embodiments, the steering mechanism can comprise at least four pullwires wherein two of the at least four pullwires are attached to the guide catheter in diametrically opposed locations and another two of the at least four pullwires are attached to the guide catheter in diametrically opposed locations. In other words, the catheter may include two sets of pullwires, each set functioning in an opposing manner as described. When the two sets of pullwires are positioned so that each pullwire is 90 degrees apart, the catheter may be curved so that the distal end is directed from side to side and up and down. In other embodiments, the steering mechanism comprises at least three pullwires, each pullwire symmetrically positioned approximately 120 degrees apart. When tension is applied to any of the pullwires individually, the catheter is curved in the direction of the pullwire under tension. When tension is applied to two pullwires simultaneously, the catheter is curved in a direction between the pullwires under tension. Additional directions may also be achieved by various levels of tension on the pullwires. It may be appreciated that any number, combination and arrangement of pullwires may be used to direct the catheters in any desired direction.

In some embodiments, a portion of guide catheter 105 can comprise one or more articulating members. In this case, the at least one pullwire is attached to one of the articulating members so that the curve is formed by at least some of the articulating members. Each pullwire is attached to the catheter at a location chosen to result in a particular desired curvature of the catheter when tension is applied to the pullwire. For example, if a pullwire is attached to the most distal articulating member in the series, applying tension to the pullwire will compress the articulating members proximal to the attachment point along the path of the pullwire. This results in a curvature forming in the direction of the pullwire proximal to the attachment point. It may be appreciated that the pullwires may be attached to any location along the catheter and is not limited to attachment to articulating members. Typically, the articulating members comprise interfitting domed rings but may have any suitable shape.

It may also be appreciated that curves in guide catheter 105 may be formed by any combination of mechanisms. For example, a portion of guide catheter could form a curve by shape memory material, while a different portion of guide catheter could form a curve by actuation of a steering mechanism.

The steering mechanisms may be actuated by manipulation of actuators located on handle 110. The handle 110 can be connected with the proximal end of the guide catheter 105 and remains outside of the body. One or more actuators or controls 120 can be provided on handle 110 and may have any suitable form, including buttons, levers, knobs, switches, toggles, dials, or thumbwheels, to name a few. When pullwires are used, each actuator may apply tension to an individual pullwire or to a set of pullwires. The handle may also include one or more locking mechanisms (not shown in the figures) configured to interface with, and selectively lock into place, one or more of the controls 120.

In at least one embodiment, the handle 110 includes at least one control 120 for actuating and/or adjusting one or more components of a cutting mechanism 130. As shown in FIG. 1, the cutting mechanism 130 is configured to extend beyond the distal end 115 of the guide catheter 105. In at least one embodiment, the cutting mechanism 130 is routable through the guide catheter 105 and retractable into the guide catheter 105. The at least one control 120 may control the cutting mechanism's 130 extension from and retraction into the guide catheter 105. Additionally, or alternatively, the at least one control 120 may be configured to provide selective actuation of the cutting mechanism 130.

The at least one control 120 may be operatively connected to one or more additional elements of the cutting mechanism 130. The cutting mechanism 130 is shown here in generic form as a dashed line, and therefore represents any of the cutting mechanism 130 embodiments described herein.

Figure 2:
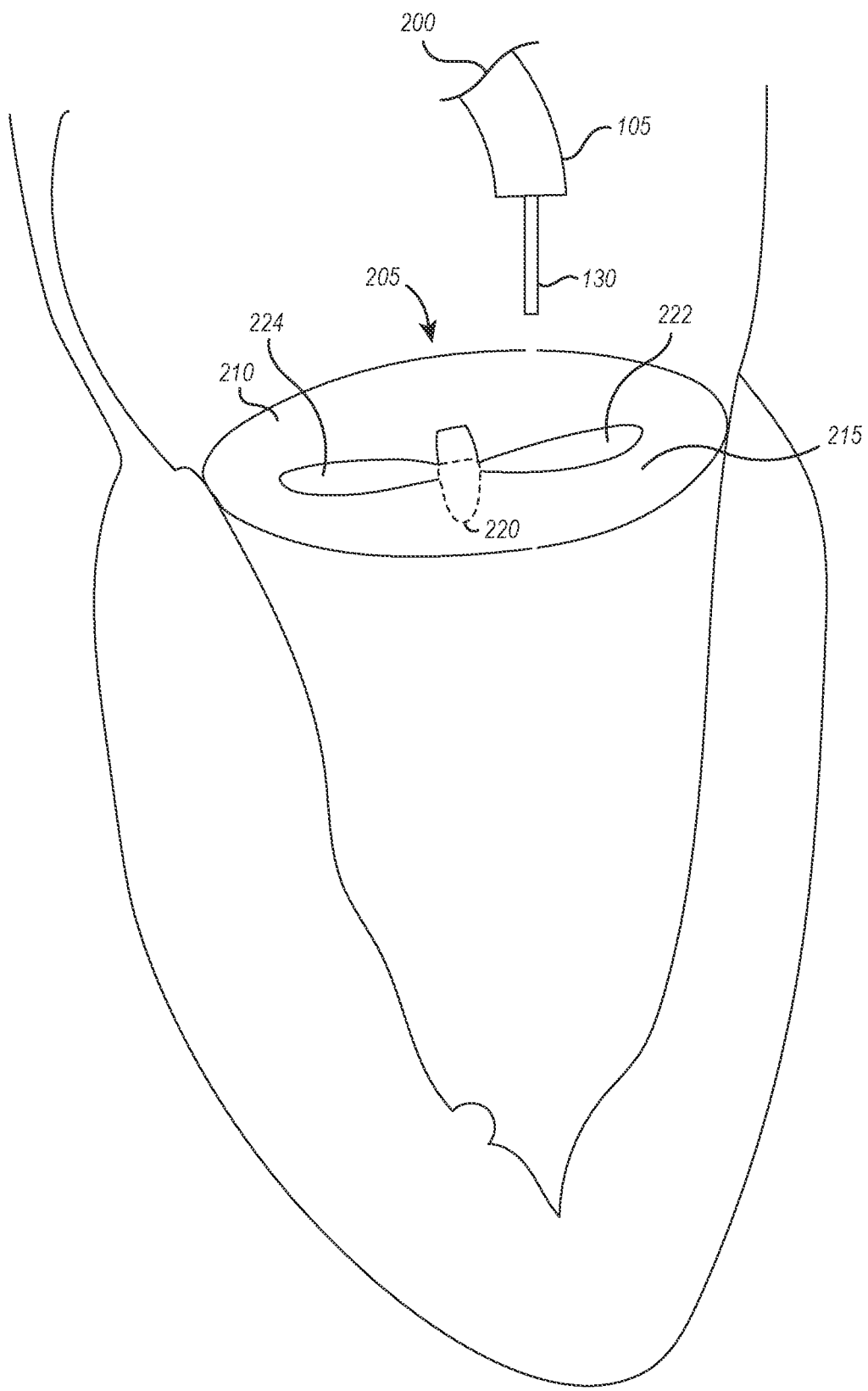
FIG. 2 is perspective view of an embodiment of a cutting mechanism according to the present disclosure shown in use in association with a human heart.

FIG. 2 is a perspective view of an exemplary embodiment of a cutting mechanism shown in use in association with a human heart, specifically the mitral valve 205. The mitral valve 205 comprises an anterior mitral leaflet 210 and a posterior mitral leaflet 215. FIG. 2 also shows an interventional implant (e.g., MitraClip®) 220, which has previously been affixed to the leaflets in an effort to reduce regurgitation. As shown, the affixation of implant 220 to the leaflets creates a first orifice 222 and a second orifice 224 located on opposing sides of implant 220 and between the anterior mitral leaflet 210 and the posterior mitral leaflet 215. And, as discussed above, if further treatment is required in the form of the installation of an artificial, replacement mitral valve, the prior clip implant 220 must be detached from one or both of the leaflets before the replacement valve can be implanted.

As further illustrated in FIG. 2, the distal end 115 of the guide catheter 105 can extend through an interatrial septum 200 of the heart. Once the distal end 115 of guide catheter 105 is properly positioned above the mitral valve 205, cutting mechanism 130 may be advanced to extend beyond the distal end 115 of guide catheter 110. In at least one embodiment, cutting mechanism 130 is configured to extend from the distal end 115 of the guide catheter 105 through the first orifice 222 of the mitral valve 205 (from an atrial side to a ventricle side), as shown in FIG. 2. One skilled in the art will appreciate that the positioning of the guide catheter 105 and cutting mechanism 130 in FIG. 2 is merely exemplary and the present invention is not limited to the positioning shown.

Figure 3B:
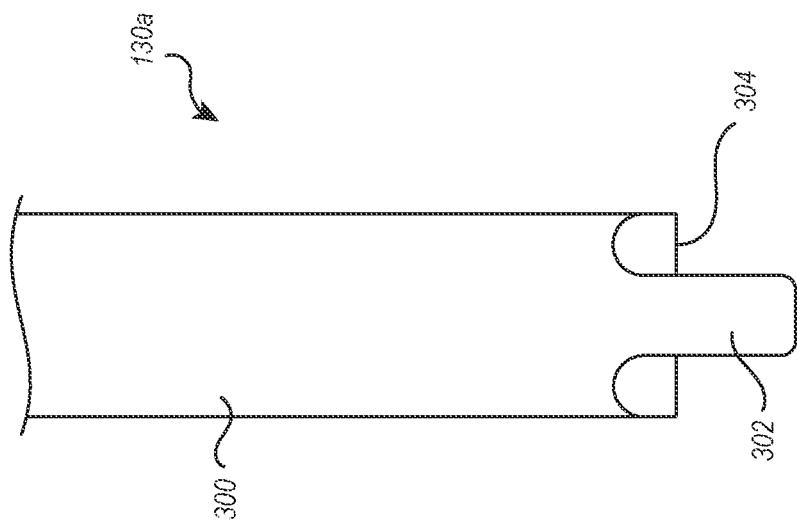
FIGS. 3A-3B illustrate a first embodiment of a cutting mechanism according to the present disclosure.
Figure 3A:
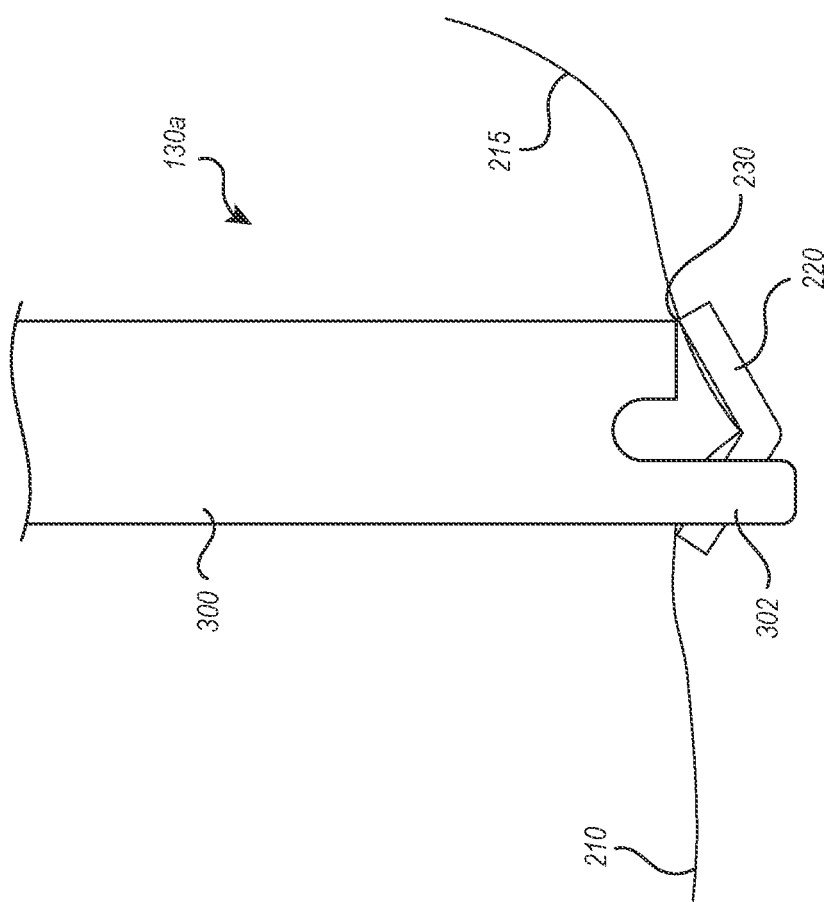

FIGS. 3A-3B illustrate a first embodiment of a cutting mechanism, designated as 130a. As shown, the cutting mechanism 130a may comprise an elongate inner catheter or shaft 300, extending from a proximal end (not shown in FIG. 3) to a distal end of the leaflet cutting system 100. The proximal end of the cutting mechanism 130a can be operatively coupled to the handle 110, and handle 110 provided with controls adapted to manipulate the cutting mechanism 130a, including advancing, retracting and/or rotating the cutting mechanism 130a relative to the guide catheter 105.

As shown in FIGS. 3A-3B, cutting mechanism 130a is positioned within the interior of guide catheter 105 during advancement and positioning of the system 100 above the mitral valve 205. As discussed below, once the distal end 115 of guide catheter 105 is properly positioned above the mitral valve 205 and in proper alignment with interventional implant 220, the handle 110 can be manipulated to cause cutting mechanism 130a to advance relative to guide catheter 105 and to pass through one of the orifices 222, 224 of the mitral valve 205, and then further manipulated to cause the cutting mechanism to slice through the tissue of one of the leaflets 210, 215, thereby cutting the affected leaflet and separating the interventional implant 220 from the affected leaflet.

FIG. 3A is a side perspective view showing the cutting mechanism 130a in use within a mitral valve 205 having an anterior mitral leaflet 210 and a posterior mitral leaflet 215. An interventional implant (e.g., MitraClip®) 220 approximates the adjacent leaflets 210 and 215. As shown in FIG. 3A, the cutting mechanism may comprise an inner catheter or shaft 300 having a proximal and distal end. The shaft 300 may be configured to extend from and retract into the distal end 115 of the guide catheter 105. In at least one embodiment the shaft 300 can comprise a hypotube. The distal end of the shaft 300 may comprise a stabilizing extension 302 configured to secure the interventional implant 220 when the shaft 300 is extended distally and the extension 302 engages with the mitral valve. The distal end of the shaft 300 may also comprise an opposing cutting edge 304 configured to cut a portion of leaflet tissue of the mitral valve. With the extension 302 in contact with the implant 220, shaft 300 can be rotated, thereby causing cutting edge 304 to cut an arcuate path through the leaflet tissue adjacent the implant 220 from first orifice 222 to second orifice 224. One skilled in the art will appreciate that the positioning in FIG. 3A is merely exemplary and the invention is not limited to the positioning shown.

The guide catheter is not shown in FIGS. 3A-3B, but it should be understood that cutting mechanism 130a is intended for use within a suitable guide catheter, such as that discussed above, to position the distal end of cutting mechanism 130a above the interventional device 220. Once properly positioned, shaft 300 can be advanced relative to the guide catheter so as to extend beyond the distal end of the guide catheter. With the shaft 300 advanced, the entire system can be advanced distally, until the distal end of stabilizing extension 302 engages the fold of leaflet tissue located opposite the interventional clip 220, which fold is created when the anterior and posterior leaflets 210 and 215 are brought and held together by interventional device 220. Once in that position, shaft 300 can be rotated to cause the cutting edge 304 to scribe an arc across the leaflet tissue from one orifice 222 to the other orifice 224, thereby cutting the leaflet tissue and separating the affected leaflet from the interventional device 220.

In at least one embodiment, the cutting mechanism 130 further comprises a wire (not shown) that extends from the handle 110 to the cutting edge 304, the wire configured to selectively provide electrosurgical energy to the portion of leaflet tissue of the mitral valve via the cutting edge 304. The cutting edge 304 may comprise a material with low impedance, such as platinum iridium, silver, gold, or a combination thereof. In at least one embodiment, the excision edge 304 comprises a sharp edge or other cutting means. Thus, cutting of the leaflet tissue by cutting edge 304 may be accomplished through mechanical cutting by cutting edge 304, by the application of electrosurgical energy through cutting edge 304, or by a combination of both.

Although FIG. 3A shows the cutting edge 304 positioned on the posterior mitral leaflet 215, in at least one embodiment the cutting mechanism 130a can be configured and/or utilized to cut a portion of anterior mitral leaflet 210. In either case, the interventional implant 220 may remain attached to the posterior mitral leaflet 210 thereby reducing the risk that the interventional implant 200 will interfere with functioning of the left ventricular outflow tract. Additionally, or alternatively, the posterior mitral leaflet 210 may be cut with little or acceptable risk of left ventricular outflow tract interference. In at least one embodiment, both leaflets can be cut and the interventional implant 200 removed from the patient via the leaflet cutting system 100.

FIG. 3B is a front perspective view of the cutting device 130a. As shown, the extension 302 extends distally past a distal end of the cutting edge 304. One skilled in the art will appreciate that the cutting mechanism 130a is not limited to that shown in FIGS. 3A-3B. Neither the extension 302 nor the cutting edge 304 is limited to the size or shape as illustrated.

In this and other embodiments described herein, inner catheter or hypotube 300 should preferably have sufficient flexibility as to be able to conform to bends formed by guide catheter 105. Additional flexibility to accommodate bending may be provided in certain regions of hypotube 300 by a series of laser cuts formed in the outer wall of hypotube 300. In addition, hypotube 300 should also provide sufficient compressive and tensile strength to permit forces to be transmitted through hypotube 300, from the proximal end to the distal end, sufficient to facilitate advancement and retraction of hypotube 300 relative to guide catheter 105 Further still, hypotube 300 should provide sufficient torqueability to allow a rotational force applied through one or more controls at the proximal end of system 100 to be transmitted through the length of hypotube 300 to facilitate rotation of hypotube 300 to effectuate cutting of leaflet tissue.

Figure 4A:
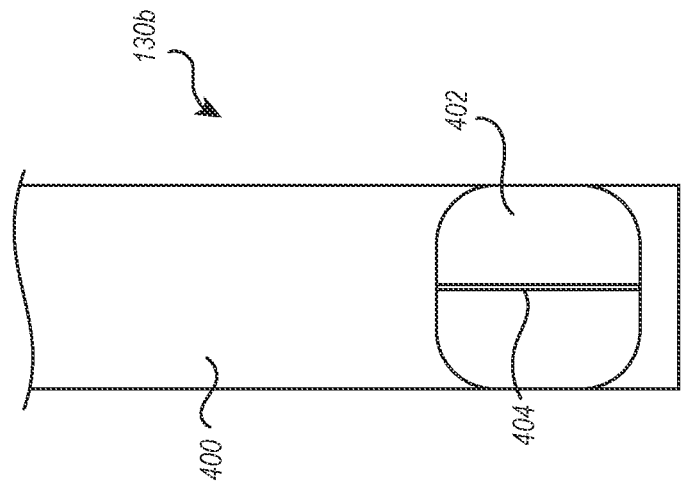
FIGS. 4A-4C illustrate a second embodiment of a cutting mechanism according to the present disclosure.
Figure 4B:
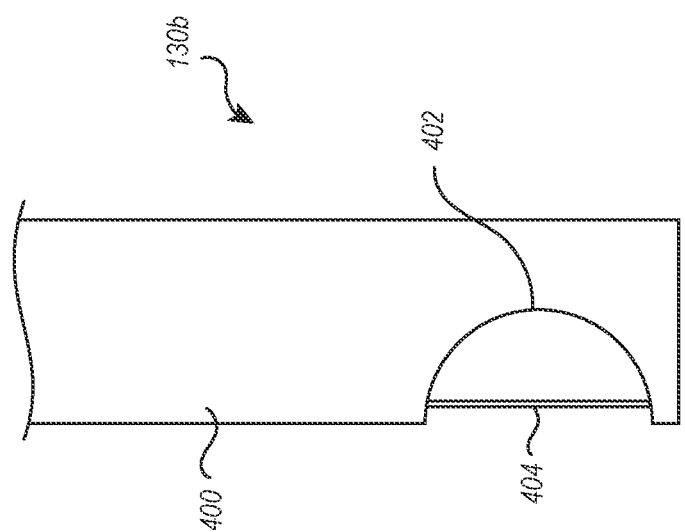
Figure 4C:
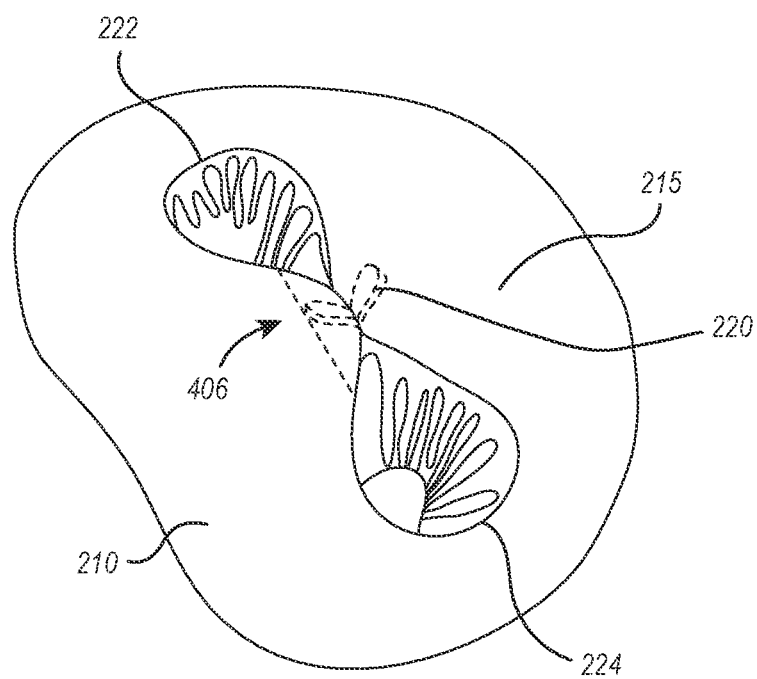

FIGS. 4A-4C illustrate a second embodiment of a cutting mechanism, designated as 130b. FIG. 4A is a side perspective view, and FIG. 4B is a front perspective view of the cutting mechanism 130b. Here, again, the guide catheter is not shown in FIGS. 4A-4B, but it should be understood that cutting mechanism 130b is intended for use within a suitable guide catheter, such as that discussed above, to position the distal end of cutting mechanism 130b above the interventional device 220.

As shown, the cutting mechanism 130b may comprise a shaft 400 having a proximal end and a distal end. The distal end of the shaft 400 can include a cutout area 402, with a cutting wire 404 that extends in an axial direction across the cutout 402. The height of cutout 402 should preferably be somewhat larger than the thickness of the leaflet tissue that is to be cut.

The shaft 400 may be configured to extend from the distal end 115 of the guide catheter 105. In at least one embodiment, the shaft 400 is configured to be selectively advanced beyond the distal end 115 of the guide catheter 105 into a first orifice 222 of the mitral valve 205. The guide catheter 105 may then be manipulated to move the shaft 400 in a transverse direction to bring cutting wire 404 into contact with leaflet tissue.

The cutting wire 404 may be configured to selectively provide electrosurgical energy to the portion of leaflet tissue of the mitral valve, thereby cutting the portion of leaflet tissue. In at least one embodiment, cutting wire 404 can comprise a material with low impedance, such as platinum iridium, silver, gold, or a combination thereof. Additionally, or alternatively, the cutting wire 404 can include a sharpened edge. The at least one control 120 may be configured to advance the shaft 400 along a horizontal plane, thereby cutting the portion of the leaflet tissue along the horizontal plane 406, as shown in FIG. 4C.

One skilled in the art will appreciate that the shaft 400, cutout area 402, and cutting wire 404 shown in FIGS. 4A-4B are merely exemplary, and the invention is not limited to the cutting mechanism 130b as illustrated. Further, although FIG. 4C illustrates the horizontal plane cutting path 406 on a portion of the anterior mitral leaflet 210, in at least one embodiment the posterior mitral leaflet 215 is cut. Further, the interventional implant 220 may be removed from the patient by cutting both leaflets 210 and 215.

One skilled in the art will appreciate that the present invention is not limited to use within the mitral valve. The cardiac valve could also be the tricuspid aortic, pulmonic valve, etc. More generally, the embodiments described herein may be applied in other implementations involving removal of a previously implanted or deployed device from tissue. Further, any suitable delivery approach may be used, including transseptal, transfemoral, radial, transjugular, or transapical.

In describing the various embodiments above, the description may at times have explicitly discussed one particular mitral valve leaflet, such as anterior leaflet 210. It should be understood and appreciated, however, that the invention is not intended to be limited to either specific leaflet, but instead can be used to cut either anterior leaflet 210, posterior leaflet 215, or both.

It should also be understood that the order of manipulation of components of the various embodiments as described above are provided as representative examples only, and changes in the order of manipulation that may be readily understood by those skilled in the art are intended to be encompassed within the scope of this disclosure.

Further still, in addition to the embodiments described above, it should also be understood that individual components from one embodiment could also be combined with and/or substituted for a comparable component described in a different embodiment.

Similarly, while many of the embodiments discussed above contemplate mechanical cutting of leaflet tissue by means of sharpened edges of a cutting element, it should be further understood that such embodiments could also be adapted to include suitable electrical connections between the cutting element and a source of electrosurgical energy so that such cutting elements may accomplish cutting of tissue by mechanical cutting, by the application of electrosurgical energy to surrounding tissue through the cutting element, or by a combination of both.

Also, with any or all of the foregoing embodiments, one or more components of the leaflet cutting system can also include one or more radiopaque and/or echogenic markers to aid in the visualization of such components during a procedure. For example, one or more radiopaque and/or echogenic markers can be provided on the distal end 115 and/or the steerable portion 117 of the guide catheter 105. Similarly, one or more radiopaque and/or echogenic markers can also be provided on various components of the different embodiments of the cutting mechanisms described above, including, but not limited to, such markings being provided on the distal ends of the inner catheter, hypotube, cutting blades, stabilizing extension, etc.

One skilled in the art will appreciate that the present invention is not limited to use within the mitral valve. The cardiac valve could also be the tricuspid aortic, pulmonic valve, etc. More generally, the embodiments described herein may be applied in other implementations involving removal of a previously implanted or deployed device from tissue. Further, although the figures show the guide catheter 105 extending through the interatrial septum 200, the present invention is not limited to use via a transseptal approach. Any suitable delivery approach may be used, including transfemoral, radial, transjugular, or transapical.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Following are some further example embodiments of the invention. These are presented only by way of example and are not intended to limit the scope of the invention in any way.

Embodiment 1. A device for cutting leaflet tissue at a cardiac valve, comprising: a guide catheter having a proximal end and a distal end, the guide catheter being positionable at a cardiac valve, a cutting mechanism routable through the guide catheter and configured to extend from the distal end of the guide catheter, the cutting mechanism configured to cut a portion of leaflet tissue of the cardiac valve, and a handle coupled to the proximal end of the guide catheter, the handle comprising at least one control operatively connected to the cutting mechanism such that the at least one control is configured to provide selective actuation of the cutting mechanism.

Embodiment 2. The device of embodiment 1, wherein the guide catheter is positionable at the cardiac valve transseptally or transapically.

Embodiment 3. The device in any of embodiments 1 to 2, wherein the cutting mechanism comprises an extension configured to secure an interventional implant and an opposing excision edge configured to cut the portion of leaflet tissue of the cardiac valve.

Embodiment 4. The device in any of embodiments 1-3, wherein the extension extends distally past a distal end of the excision edge.

Embodiment 5. The device in any of embodiments 1-4, wherein the cutting mechanism further comprises a wire that extends from the handle to the excision edge, the wire configured to selectively provide radio frequency current energy to the portion of leaflet tissue of the cardiac valve via the excision edge.

Embodiment 6. The device in any of embodiments 1-5, wherein the excision edge comprises a material with low impedance.

Embodiment 7. The device in any of embodiments 1-6, wherein the excision edge comprises platinum iridium, silver, gold, or a combination thereof.

Embodiment 8. The device in any of embodiments 1-7, wherein: the cutting mechanism comprises a shaft having a proximal end and a distal end, the cutting mechanism comprises a cutting wire disposed within the shaft, the distal end of the shaft comprises a cutout area that exposes a portion of the cutting wire disposed within the shaft, and the shaft is configured to extend from the distal end of the guide catheter through a first orifice of the cardiac valve thereby engaging the cutting wire with leaflet tissue.

Embodiment 9. The device in any of embodiments 1-8, wherein the cutting wire is configured to selectively provide radio frequency current energy to the portion of leaflet tissue of the cardiac valve thereby cutting the portion of leaflet tissue.

Embodiment 10. The device in any of embodiments 1-9, wherein the cutting wire comprises a material with low impedance.

Embodiment 11. The device in any of the embodiments 1-10, wherein the cutting wire comprises platinum iridium, silver, gold, or a combination thereof.

Embodiment 12. The device in any of embodiments 1-11, wherein the cutting wire comprises a sharp edge.

Embodiment 13. The device in any of embodiments 1-12, wherein the shaft is configured to advance along a horizontal plane thereby cutting the portion of the leaflet tissue along the horizontal plane.

Embodiment 14. A system for cutting leaflet tissue at a cardiac valve, comprising, a guide catheter having a proximal end and a distal end, wherein the distal end of the guide catheter is guided to a position at a cardiac valve; a cutting mechanism having a proximal end and a distal end, wherein the cutting mechanism is routable through the guide catheter and configured to extend beyond the distal end of the guide catheter and retract into the guide catheter, wherein the cutting mechanism is configured to cut a portion of leaflet tissue of the cardiac valve.

Embodiment 15. The system of embodiment 14, wherein the cutting mechanism comprises an extension configured to secure an interventional implant and an opposing excision edge configured to cut the portion of leaflet tissue of the cardiac valve.

Embodiment 16. The system in any of embodiments 14-15, wherein the extension extends distally past a distal end of the excision edge.

Embodiment 17. The system in any of embodiments 14-16, wherein the cutting mechanism further comprises a cutting wire that extends from the proximal end of the guide catheter to the excision edge, the cutting wire configured to selectively provide radio frequency current energy to the portion of leaflet tissue of the cardiac valve via the excision edge.

Embodiment 18. The system in any of embodiments 14-17, wherein: the cutting mechanism comprises a shaft having a proximal end and a distal end, the cutting mechanism comprises a cutting wire disposed within the shaft, the distal end of the shaft comprises a cutout area that exposes a portion of the wire disposed within the shaft, and the shaft is configured to extend from the distal end of the guide catheter through a first orifice of the cardiac valve thereby engaging the cutting wire with leaflet tissue.

Embodiment 19. The system in any of embodiments 14-18, wherein the cutting wire is configured to selectively provide radio frequency current energy to the portion of leaflet tissue of the cardiac valve thereby cutting the portion of leaflet tissue.

Embodiment 20. The system in any of embodiments 14-19, wherein the cutting wire comprises a sharp edge.

Embodiment 21. The system in any of embodiments 14-20, wherein the shaft is configured to advance along a horizontal plane thereby cutting the portion of the leaflet tissue along the horizontal plane.

Embodiment 22. A method of cutting cardiac valve tissue at a cardiac valve within a body, comprising: positioning a guide catheter, having a proximal and a distal end such that the distal end of the guide catheter is positioned at a cardiac valve, routing a cutting mechanism through the guide catheter such that the cutting mechanism extends distally beyond the distal end of the guide catheter, wherein the cardiac valve is associated with an interventional implant that approximates adjacent leaflets of the cardiac valve, and a cutting mechanism extends from the guide catheter, and actuating the cutting mechanism to cut at a portion of least one leaflet of the approximated adjacent leaflet.

Embodiment 23. The method of embodiment 22, wherein actuating the cutting mechanism comprises delivering radio frequency current energy through the cutting mechanism.

We claim:

1. A device for cutting leaflet tissue at a cardiac valve, comprising:
   a guide catheter having a proximal end and a distal end, the guide catheter being positionable at a cardiac valve;
   a cutting mechanism routable through the guide catheter and configured to extend from the distal end of the guide catheter, the cutting mechanism configured to cut a portion of leaflet tissue of the cardiac valve, wherein the cutting mechanism comprises:
     a stabilizing extension configured to make contact with an interventional implant, and an opposing excision edge configured to cut the portion of leaflet tissue of the cardiac valve, wherein the extension extends distally past a distal end of the excision edge, wherein the stabilizing extension provides an axis of rotation about which the opposing excision edge rotates to cut the portion of the leaflet tissue; and a handle coupled to the proximal end of the guide catheter, the handle comprising at least one control operatively connected to the cutting mechanism such that the at least one control is configured to provide selective actuation of the cutting mechanism.

2. The device of claim 1, wherein the guide catheter is positionable at the cardiac valve transseptally or transapically.

3. The device of claim 1, wherein the cutting mechanism further comprises:
a shaft having a proximal end and a distal end;
a cutting wire disposed within the shaft, wherein:
the distal end of the shaft comprises a cutout area that exposes a portion of the cutting wire disposed within the shaft, and
the shaft is configured to extend from the distal end of the guide catheter through a first orifice of the cardiac valve thereby engaging the cutting wire with leaflet tissue.

4. The device of claim 3, wherein the cutting wire comprises a sharpened edge.

5. The device of claim 3, wherein the shaft is configured to advance along a horizontal plane thereby cutting the portion of the leaflet tissue along the horizontal plane.

6. The device of claim 3, wherein the cutting wire is configured to selectively provide radio frequency current energy to the portion of leaflet tissue of the cardiac valve thereby cutting the portion of leaflet tissue.

7. The device of claim 6, wherein the cutting wire comprises a material with low impedance.

8. The device of claim 7, wherein the cutting wire comprises platinum iridium, silver, gold, or a combination thereof.

9. The device of claim 1, wherein the cutting mechanism further comprises a wire that extends from the handle to the excision edge, the wire configured to selectively provide radio frequency current energy to the portion of leaflet tissue of the cardiac valve via the excision edge.

10. The device of claim 9, wherein the excision edge comprises a material with low impedance.

11. The device of claim 10, wherein the excision edge comprises platinum iridium, silver, gold, or a combination thereof.

12. A system for cutting leaflet tissue at a cardiac valve, comprising,
a guide catheter having a proximal end and a distal end, wherein the distal end of the guide catheter is guided to a position at a cardiac valve;
a cutting mechanism having a proximal end and a distal end, wherein the cutting mechanism is routable through the guide catheter and configured to extend beyond the distal end of the guide catheter and retract into the guide catheter, wherein the cutting mechanism comprises:
a shaft having a proximal end and a distal end;
a cutout area formed in the distal end of the shaft;
a cutting wire extending across the cutout area,
wherein:
the shaft is configured to extend from the distal end of the guide catheter through a first orifice of the cardiac valve thereby engaging the cutting wire with leaflet tissue,
an extension configured to secure an interventional implant, and
an opposing excision edge configured to cut the portion of leaflet tissue of the cardiac valve, wherein the extension extends distally past a distal end of the excision edge,
wherein the cutting mechanism is configured to cut a portion of leaflet tissue of the cardiac valve.

13. The system of claim 12, wherein the cutting mechanism further comprises a cutting wire that extends from the proximal end of the guide catheter to the excision edge, the cutting wire configured to selectively provide radio frequency current energy to the portion of leaflet tissue of the cardiac valve via the excision edge.

14. The system of claim 12, wherein the cutting wire is configured to selectively provide radio frequency current energy to the portion of leaflet tissue of the cardiac valve thereby cutting the portion of leaflet tissue.

15. The system of claim 12, wherein the wire comprises a sharpened edge.

16. The system of claim 12, wherein the shaft is configured to advance along a horizontal plane thereby cutting the portion of the leaflet tissue along the horizontal plane.

17. A method of cutting cardiac valve tissue at a cardiac valve within a body, comprising:
positioning a guide catheter, having a proximal end and a distal end such that the distal end of the guide catheter is positioned at a cardiac valve;
routing an electrosurgical cutting mechanism through the guide catheter such that the electrosurgical cutting mechanism extends distally beyond the distal end of the guide catheter, wherein the cardiac valve is associated with an interventional implant that approximates adjacent leaflets of the cardiac valve, and the electrosurgical cutting mechanism extends from the guide catheter, wherein the electrosurgical cutting mechanism comprises:
a shaft having a proximal end and a distal end;
a cutting wire disposed within the shaft, wherein:
the distal end of the shaft comprises a cutout area that exposes a portion of the cutting wire disposed within the shaft, and
the shaft is configured to extend from the distal end of the guide catheter through a first orifice of the cardiac valve thereby engaging the cutting wire with leaflet tissue,
an extension configured to secure an interventional implant, and
an opposing excision edge configured to cut the portion of leaflet tissue of the cardiac valve, wherein the extension extends distally past a distal end of the excision edge; and
actuating the cutting mechanism to cut at a portion of least one leaflet of the approximated adjacent leaflet,
wherein the cutting wire provides electrosurgical energy to the portion of leaflet tissue via the opposing excision edge.

18. The method of claim 17, wherein actuating the cutting mechanism comprises delivering radio frequency current energy through the cutting mechanism.

* * * * *